US00PP23002P2

(12) United States Plant Patent
Kerley et al.

(10) Patent No.: US PP23,002 P2
(45) Date of Patent: Aug. 28, 2012

(54) ***LAVANDULA* PLANT NAMED 'KERLAVANHAZE'**

(50) Latin Name: *Lavandula angustifolia*
Varietal Denomination: KERLAVANHAZE

(76) Inventors: David Kerley, Cambridge (GB); Priscilla Grace Kerley, Cambridge (GB); Timothy Edward Kerley, Cambridge (GB)

( * ) Notice: Subject to any disclaimer, the term of this patent is extended or adjusted under 35 U.S.C. 154(b) by 303 days.

(21) Appl. No.: 12/661,871

(22) Filed: Mar. 25, 2010

(51) Int. Cl.
*A01H 5/00* (2006.01)

(52) U.S. Cl. ..... Plt./445

(58) Field of Classification Search ..... Plt./445
See application file for complete search history.

(56) References Cited

U.S. PATENT DOCUMENTS

PP9,119 P * 4/1995 Schofield ..... Plt./226

OTHER PUBLICATIONS

UPOV ROM GTITM Computer Database, GTI Jouve Retrieval Software 2011/10 Citation for 'KERLAVANHAZE'.*

* cited by examiner

*Primary Examiner* — Wendy C Haas

(57) ABSTRACT

A new and distinct *Lavandula angustifolia* cultivar named 'KERLAVANHAZE' is disclosed, characterized, a compact plant growth, producing number side-breaks, to form an overall bushy plant. Additionally the new cultivar has characteristically short peduncles, and moderately fine foliage. The new variety is a *Lavandula angustifolia*, suitable for outdoor landscape and container use.

1 Drawing Sheet

Figure 1:
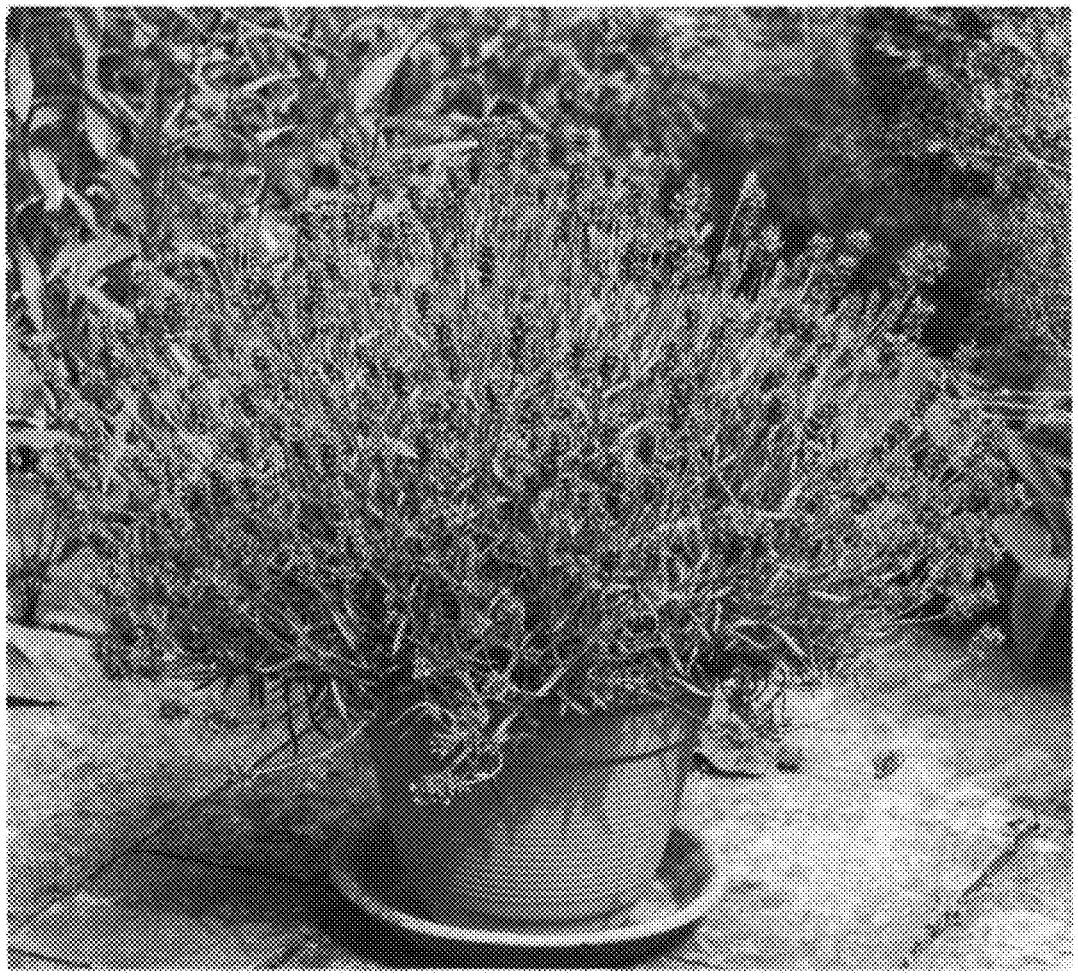

Latin name of the genus and species: *Lavandula angustifolia.*

Variety denomination: 'KERLAVANHAZE'.

BACKGROUND OF THE INVENTION

The new cultivar is the product of a planned breeding program under the direction of the inventors, David Kerley, Priscilla Kerley and Timothy Kerley, all citizen of the United Kingdom. The objective of the breeding program was to produce new *Lavandula angustifolia* cultivars for commercial ornamental purposes. The breeding program consisted of organizing groups of unnamed, unpatented commercial *Lavandula angustifolia* varieties for open pollination. The seeds from these unnamed parents were collected and planted out, resulting in the selection of the new variety 'Kerlavanhaze' in the Spring of 2001. The breeding program and selection all took place at a commercial nursery in Cambridge, the United Kingdom.

Asexual reproduction of the new cultivar 'KERLAVANHAZE' by vegetative cuttings was first performed in Cambridge, UK in the Autumn of 2001 and has shown that the unique features of this cultivar are stable and reproduced true to type in successive generations.

SUMMARY OF THE INVENTION

The cultivar 'KERLAVANHAZE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERLAVANHAZE' These characteristics in combination distinguish 'KERLAVANHAZE' as a new and distinct *Lavandula* cultivar:

1. Compact plant growth.
2. Short peduncles.
3. Numerous side breaks, forming a bushy overall plant.
4. Moderately fine foliage.
5. Pale lavender-blue bud coloration.

COMMERCIAL COMPARISON

Plants of the new cultivar 'KERLAVANHAZE' are similar to plants of the unpatented variety *Lavandula angustifolia* 'Hidcote' in most horticultural characteristics, however, plants of the new cultivar 'KERLAVANHAZE' are consistently overall more compact than 'Hidcote' with an overall more controlled growth habit more suitable for small commercial pots. Additionally, 'KERLAVANHAZE' produces a shorter, broader flowering spike, a lighter flower bud color on a stronger peduncle. Finally, foliage of 'KERLAVANHAZE' is narrower and shorter than foliage of 'Hidcote.'

Plants of the new cultivar 'KERLAVANHAZE' can also be compared to the commercial variety *Lavandula angustifolia* 'Blue Cushion' U.S. Plant Pat. No. 9,119. Plants of 'KERLAVANHAZE' are similar to plants of 'Blue Cushion' in most horticultural characteristics, however, plants of the new cultivar have a shorter, thicker peduncle, with a broader, denser flower spike. Additionally, the flower bud color of 'KERLAVANHAZE' is darker than the flower buds of 'Blue Cushion'

BRIEF DESCRIPTION OF THE PHOTOGRAPH

The accompanying photograph in FIG. 1 illustrates in full color typical plants of 'KERLAVANHAZE' grown outdoors in Cambridge, UK. Plants are approximately 8 months old shown in an approximately 4 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'KERLAVANHAZE' plants grown outdoors in Cambridge, UK. The growing temperature ranged from approximately 0 to 10° C. at night to 10 to 20° C. during the day. Measurements and numerical values represent averages of typical flowering types. No chemical or photoperiodic treatments were given.

Botanical classification: *Lavandula angustifolia* cultivar 'KERLAVANHAZE.'

Age of the plant described: Approximately 8 months, in an 11 cm pot.

PROPAGATION

Time to rooting: About 20 days at approximately 20° C.

Root description: Fine, well branched, becoming woody with age.

PLANT

Growth habit: Upright, bushy, aromatic perennial.
Height: Approximately 17.5 cm.
Plant spread: Approximately 15.6 cm.
Branching characteristics: Moderate branching.
Diameter of lateral branches: Approximately 0.2 cm.
Texture of lateral branches: Pubescent.
Internode length: Approximately 1 cm, highly variable.
Strength of stem: Strong.
Color of lateral branches: A color between RHS Yellow-Green 146A and 146B.
Number of leaves per lateral branch: Approximately 16.

FOLIAGE

Leaf:
- *Arrangement*.—Opposite, simple.
- *Average length*.—Approximately 4.4 cm.
- *Average width*.—Approximately 0.53 cm.
- *Shape of blade*.—Narrowly oblanceolate.
- *Apex*.—Acute.
- *Base*.—Cuneate.
- *Attachment*.—Sessile.
- *Margin*.—Entire.
- *Texture of top surface*.—Pubescent.
- *Texture of bottom surface*.—Pubescent.
- *Color*.—Mature foliage upper side: Between RHS Yellow-Green 147A and Green 137A. Mature foliage under side: Between RHS Yellow-Green 147B.
- *Venation*.—Type: One very prominent mid-vein, with a fine network of much smaller veins. Venation color upper side: Between RHS Yellow-Green 147A and Green 137A, indistinguishable from foliage coloration. Venation color under side: Near RHS Yellow-Green 144A.

Petiole: Not present.

FLOWER

Bloom period: Naturally blooming profusely early June through mid-Summer.

Inflorescence:
- *Form*.—Small single flower in verticillasters arranged in spikes. Flowers have bracts. Corolla tube has 2 upper-lips and 3 lower lips.
- *Flower spikes*.—Height: Approximately 3 cm. Diameter: Approximately 1.075 cm. Spacing between bottom florets: Average 1.0 cm.

Flower bud:
- *Bud color*.—Near RHS Violet 87A to 88B.
- *Bud height*.—Approximately 5-6 mm.
- *Bud width*.—Approximately 2.0-2.5 mm.

Individual flower:
- *Corolla-length of upper lobes* (2).—Approximately 5 mm.
- *Corolla-length of lower lobes* (3).—Approximately 3-3.5 mm.
- *Corolla-width of upper lobes*.—Approximately 4.0 mm.
- *Corolla-width of lower lobes*.—Approximately 2 mm.
- *Shape of upper lobes*.—2 conjoined lobes.
- *Shape of lower lobes*.—3 smaller lobes, fused at the base.
- *Apex of upper lobes*.—Blunt, rounded.
- *Apex of lower lobes*.—Acute rounded.
- *Texture of corolla—upper surface*.—Savoyed.
- *Texture of corolla—lower surface*.—Slightly savoyed.
- *Color when opening—upper surface*.—Near RHS Violet87C.
- *Color when opening—lower surface*.—Near RHS Violet 87C.
- *Color fully open*.—Near RHS Violet 87A and 87B.
- *Inflorescence bracts* (3 *buds subtend from each bract*).—Approximately 4 mm long×3.5 mm wide.
- *Bract color*.—Near RHS Greyed-Orange 164D, veins 165A.
- *Calyx arrangement*.—Tube.
- *Calyx width*.—Approximately 2-3 mm.
- *Sepal length*.—Approximately 5-6 mm.
- *Sepal texture*.—Very hirsute, hairs same colour as sepal.
- *Sepal colour—flower opening*.—Near RHS Violet 86A, base near Yellow-Green 144B.
- *Sepal colour—fully open*.—Near RHS Violet 86A, base near Yellow-Green 144C.

Peduncle:
- *Peduncle length*.—Approximately 6.2 cm.
- *Peduncle diameter*.—Approximately 1.5 cm.
- *Aspect*.—Upright.
- *Color*.—Near RHS Yellow-Green 146B.
- *Texture*.—Pubescent.

REPRODUCTIVE ORGANS

- *Filament length*.—1.5 mm.
- *Anther length*.—0.6 mm.
- *Anther color*.—167D.
- *Pollen color*.—23A.
- *Pollen amount*.—Moderate-plentiful.
- *Pistil length*.—7 mm.
- *Style length*.—4-4.5 mm.

*Style color*.—155B.
*Stigma color*.—150D.

OTHER CHARACTERISTICS

Fragrance: Strong *Lavandula* scent, both flowers and foliage.
Disease resistance: Neither resistance nor susceptibility to diseases or pests has been observed in this variety.
Drought tolerance and cold tolerance: Hardy perennial. Tolerates high temperature to at least 32° C. Tolerates low temperatures to −°12 C. While specific drought tolerance has not been observed, once plants are established very little water is necessary to maintain plants.
Fruit/seed production: Fruit and seed production not observed.

What is claimed is:

1. A new and distinct cultivar of *Lavandula* plant named 'KERLAVANHAZE' as herein illustrated and described.

* * * * *